United States Patent [19]

Imade et al.

[11] Patent Number: 4,880,011

[45] Date of Patent: Nov. 14, 1989

[54] ULTRASONIC ENDOSCOPE APPARATUS

[75] Inventors: Shinichi Imade; Kazunori Shionoya; Eishi Ikuta; Koji Taguchi; Toyoo Nishiyama; Seiichi Wakamatsu, all of Hachioji; Tatsuo Nagasaki, Yokohama, all of Japan

[73] Assignee: Olympus Optical Co., Ltd., Tokyo, Japan

[21] Appl. No.: 186,171

[22] Filed: Apr. 26, 1988

[30] Foreign Application Priority Data

Apr. 30, 1987 [JP] Japan ................................. 62-106746

[51] Int. Cl.$^4$ ............................................. A61B 8/12
[52] U.S. Cl. .................................... 128/662.06; 128/4
[58] Field of Search ...................... 128/660.09, 660.10, 128/662.06; 73/620, 633

[56] References Cited

U.S. PATENT DOCUMENTS

| 4,494,549 | 1/1985 | Namba et al. | 128/662.06 |
| 4,579,122 | 4/1986 | Shiniza et al. | 128/660.1 X |
| 4,671,292 | 6/1987 | Matzuk | 128/660.09 |
| 4,674,515 | 6/1987 | Andou et al. | 128/662.06 |

Primary Examiner—Francis Jaworski
Attorney, Agent, or Firm—Stevens, Davis, Miller & Mosher

[57] ABSTRACT

An ultrasonic endoscope apparatus in which an ultrasonic vibrating element radiating an ultrasonic wave to obtain an image of an object to be inspected is rotatably housed in a distal end of an insertion section of the endoscope, and a rotation angle sensing mechanism is also housed in the distal end. The rotation angle sensing mechanism has a magnetic recording section having a magnetization pattern for forming a magnetic field, and a magnetic sensor having at least one magneto-resistive element for sensing the magnetic field. One of the magnetic recording section and the magnetic sensor is rotated integrally with the ultrasonic vibrating element so that a rotation angle of the ultrasonic vibrating element is sensed in a precise manner.

15 Claims, 5 Drawing Sheets

FIG_1 PRIOR ART

FIG. 6
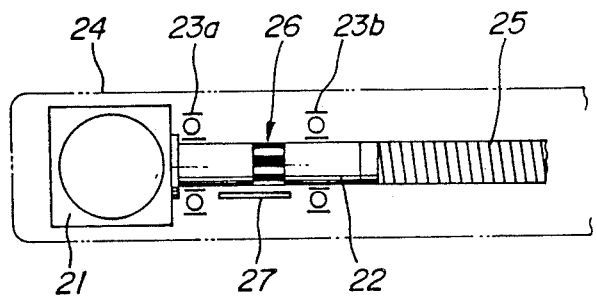
FIG. 7A
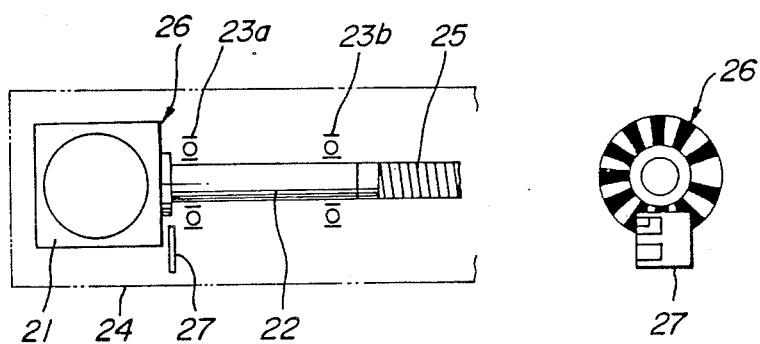
FIG. 7B

FIG_8
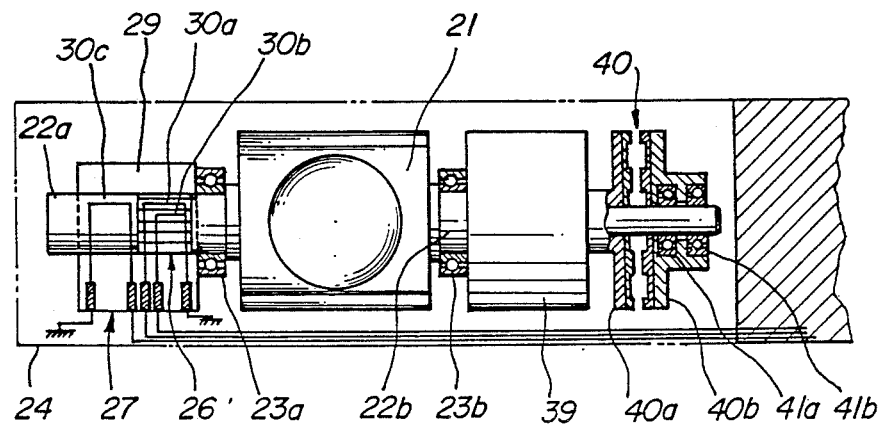

ULTRASONIC ENDOSCOPE APPARATUS

BACKGROUND OF THE INVENTION

1. Field of the Invention

The present invention relates to a mechanical radial scan type ultrasonic endoscope apparatus constructed in such a manner that an ultrasonic vibrating element provided in a distal end of an insertion section of the endoscope is rotated in the distal end.

2. Description of the Related Art

A mechanical radial scan type ultrasonic endoscope apparatus is disclosed, for example, in Japanese Patent Publication Kokai No. 60-227,740. In such a conventional endoscope apparatus, as shown in FIG. 1, the ultrasonic vibrating element 3 is rotatably supported at a distal end 2 of an insertion section 1 of the ultrasonic endoscope apparatus by pivoting a rotating shaft 4 of the ultrasonic vibrating element 3 on bearings 5a and 5b. The rotating shaft 4 of the ultrasonic vibrating element 3 is connected to one end of a flexible shaft 6 provided in the insertion section 1 and extending therethrough, and the other end of the flexible shaft 6 is connected to a motor 10 through a reduction gear mechanism 9 mounted in a sub-operation section 8 provided just below the operation section 7. The ultrasonic vibrating element 3 is rotated by the motor 10 through the reduction gear mechanism 9 and the flexible shaft 6, and a rotation angle of the ultrasonic vibrating element 3 is sensed by a rotary encoder 11 provided in the sub-operation section 8, so that a timing for transmitting an ultrasonic beam from the ultrasonic vibrating element 3 is controlled in accordance with a rotational deflection angle of the radial scanning line for forming an ultrasonic image.

In the conventional ultrasonic endoscope apparatus described above, since a rotation angle of the ultrasonic vibrating element 3 is sensed by the rotary encoder 11 provided in the sub-operation section 8, because of a torsion effect caused by an elasticity of the flexible shaft 6 or friction between the flexible shaft 6 and a wall surface of guide tube through which the flexible shaft 6 is passed, a drawback arises in that a phase shift occurs between the rotation angle sensed by the rotary encoder 11 and the actual rotation angle of the ultrasonic vibrating element 3 at the distal end 2. This phase shift is especially large when the flexible shaft 6 must be bent sharply to carry out the diagnosis. Therefore, in the conventional ultrasonic endoscope apparatus, since the rotation angle of the ultrasonic vibrating element 3 cannot be precisely sensed, the image for the diagnosis is formed by an ultrasonic beam directed in a different direction from the direction of the corresponding scanning line on the image displayed on the monitor, and thus the ultrasonic image is distorted and is not suitable for precise diagnosis.

In order to mitigate the above mentioned drawback, in Japanese Patent Publication Kokai Nos. 59-49,753, 60-90,542 and 60-111,642, there are described ultrasonic endoscope apparatuses in which a rotation angle detecting device is arranged in the distal end of insertion section. This device comprises one or two permanent magnets arranged to rotate together with the ultrasonic vibrating element or reflection mirror, and a magnetic sensing element such as coil, Hall element and magnetoresistive element for sensing the rotation of the permanent magnet. However, in these known devices, since the permanent magnet is used, the dimension of the distal end is liable to be large. Further, since only one or two permanent magnets are provided, the precision of detection of the rotation angle is low.

Moreover, in Japanese Patent Publication Kokai No. 58-21894, there is disclosed another known rotation angle detecting device in which a photo-resistive element is arranged in the distal end rotatably with the ultrasonic vibrating element and a beam spot is made incident upon the photo-resistive element, so that the rotation angle is derived by processing an output signal of the photo-resistive element which changes in accordance with a position on the element upon which the beam spot is made incident. In this device, since the photo-resistive element generates the output signal which is changed monotonously in accordance with the rotation, and therefore the rotation angle could not be sensed precisely.

Furthermore, in Japanese Patent Publication Kokai No. 59-67,942, there is shown a device comprising a ring-shaped rotary electrode, an array of dielectric material pits arranged circularly on the rotary electrode, and a stationary electrode over which said pits slide, so that the rotation angle is detected by sensing the change in the electrostatic capacitance across the rotary and stationary electrodes. In this known device, the rotation angle can be detected in a digital manner, but it is rather difficult to detect the change in the electrostatic capacitance in an accurate manner. Further, since the pits slide over the stationary electrode, mechanical wear is produced and the device could not be used for a long time.

SUMMARY OF THE INVENTION

The present invention was conceived in view of the prior art problem, and the object of the present invention is to provide an ultrasonic endoscope apparatus in which the rotation angle of the ultrasonic vibrating element can be precisely sensed so that an ultrasonic image of an object under diagnosis is always precisely displayed, while the dimension of the distal end can remain small.

The ultrasonic endoscope apparatus according to the present invention has an elongated insertion section, a distal end of which is inserted in an object to be inspected. The ultrasonic endoscope apparatus comprises an ultrasonic vibrating element rotatably housed in the distal end, means for rotating the ultrasonic vibrating element about the axis thereof, a magnetic recording section provided in the distal end, and a magnetic sensor. The ultrasonic vibrating element radiates an ultrasonic wave to obtain an image of the object; the magnetic recording section has a given pattern of magnetization for forming a magnetic field; and the magnetic sensor has at least one magnetoresistive element for sensing the magnetic field. One of the magnetic recording section and the magnetic sensor is rotated integrally with the ultrasonic vibrating element so that the magnetic sensor senses a change of the magnetic field, to thereby sense a rotation angle of the ultrasonic vibrating element. dr

BRIEF DESCRIPTION OF THE DRAWINGS

The present invention will be more fully understood from the description of the preferred embodiments of the invention set forth below, together with the accompanying drawings, in which:

FIG. 6 is a view illustrating the construction of the distal end of a second embodiment of the ultrasonic endoscope apparatus according the invention;

FIGS. 7A and 7B are views depicting the construction of the distal end of a third embodiment of the apparatus according to the invention; and FIG. 8 is a view illustrating the distal end of a fourth embodiment of the apparatus according to the present invention.

DESCRIPTION OF THE PREFERRED EMBODIMENTS

Figure 1:
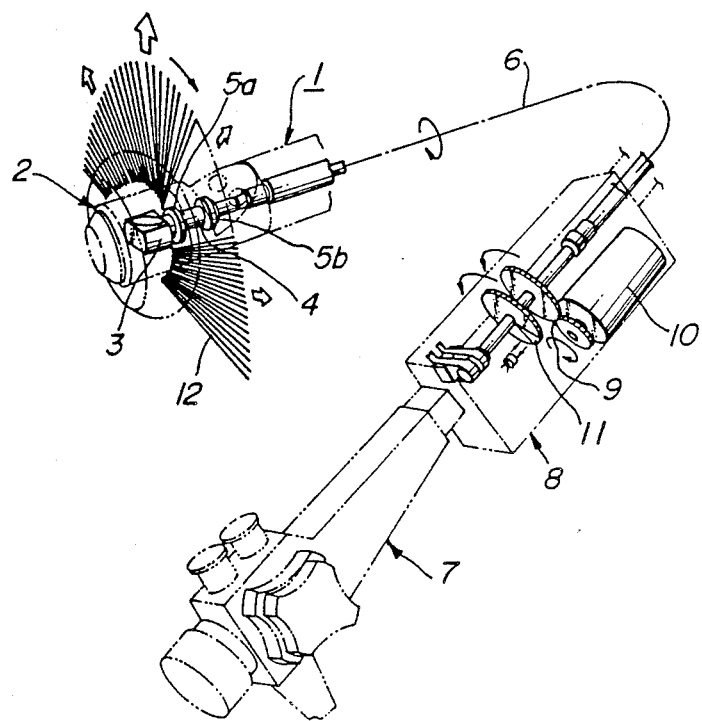
FIG. 1 is a perspective view of a prior art device.
Figure 2:
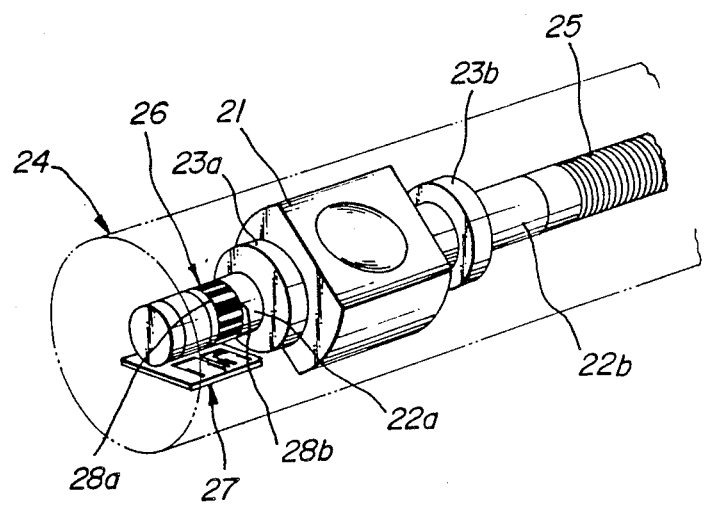
FIG. 2 is a perspective view showing the construction of a distal end of a first embodiment of the ultrasonic endoscope apparatus according to the present invention.

FIG. 2 shows the construction of a distal end of a first embodiment of the ultrasonic endoscope apparatus according to the invention. In this embodiment, an ultrasonic vibrating element 21 is provided with rotational shafts 22a and 22b coaxially projecting from both end faces of the element 21, and these rotational shafts 22a and 22b are rotatably supported by bearings 23a and 23b in a distal end 24 of the endoscope insertion section. The rotational shaft 22b is connected to one end of a flexible shaft 25 provided in the insertion section and extending therethrough, and the other end of the flexible shaft 25 is connected to a motor through a reduction gear mechanism in a suboperation section similar to the conventional device shown in FIG. 1, so that the ultrasonic vibrating element 21 is rotated by the reduction gear mechanism and the flexible shaft 25.

Figure 3:
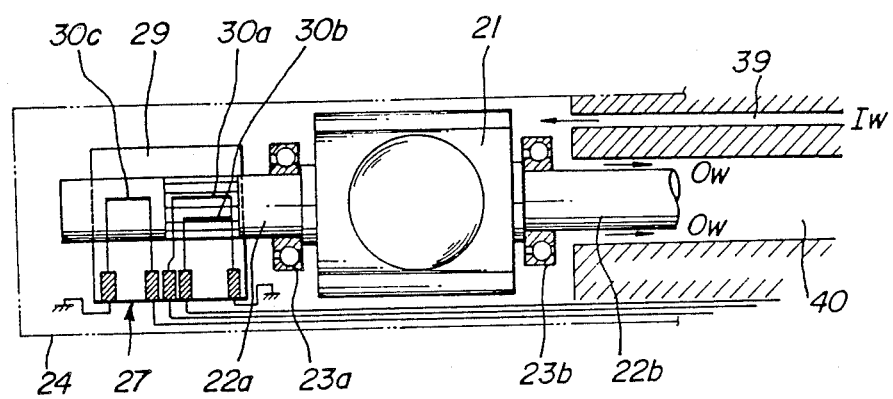
FIG. 3 is a diagrammatical plane view of the first embodiment.

In this embodiment, a magnetic recording section 26 is provided on the rotating shaft 22a rotating integrally with the ultrasonic vibrating element 21, and a magnetic sensor 27 is fixed near the magnetic recording section 26. The magnetic recording section 26 has a pattern of magnetization which is formed by uniformly coating a magnetic material on the rotating shaft 22a and magnetizing the magnetic material to alternatively form NORTH poles and SOUTH poles with a constant pitch along a rotational direction of the rotating shaft 22a. The magnetic sensor 27 is constructed, as shown in FIG. 3, by applying a magnetoresistive element (hereinafter abbreviated to MR element) made of ferromagnetic material onto a glass substrate 29 by sputtering and the like. In this embodiment, two MR elements 30a and 30b, which sense a change in the magnetic field formed by the magnetization, are provided on a portion facing the magnetic recording section 26. The two MR elements 30a and 30b are parallel to each other and are separated from each other by one and a half of the pitch of NORTH and SOUTH poles. Namely, if one MR element 30a is offset from the center of a NORTH pole in one direction by a ¼ of the pitch, the other MR element 30b is offset from the center of the adjacent SOUTH pole in the other direction by a ¼ of the pitch. A sub magneto-resistive element (hereinafter, sub MR element) 30c for sensing a drift component of an electric signal due to a temperature is provided on a portion not affected by the magnetic field of the magnetic recording portion 26.

Figure 4:
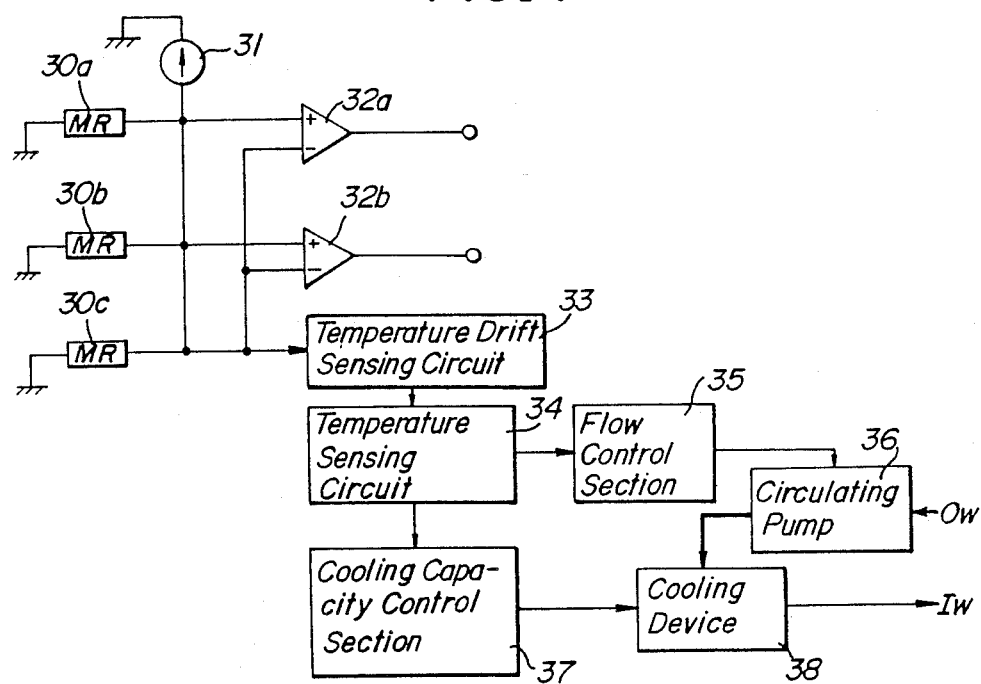
FIG. 4 is a block diagram showing a signal processing circuit in the first embodiment.

As shown in FIG. 4, the MR elements 30a, 30b, and 30c are connected in parallel to a constant current source 31, and output voltages of the MR element 30a and 30b are applied to non-inverted input terminals of differential amplifiers 32a and 32b, respectively. An output voltage of the MR element 30c is applied to inverted input terminals of the differential amplifiers 32a and 32b, respectively as well as to a temperature drift sensing circuit 33. An output of the temperature drift sensing circuit 33 is supplied to a temperature sensing circuit 34. According to an output of the temperature sensing circuit 34, a flow rate control section 35 controls a flow rate of a circulating pump 36 for circulating an ultrasonic wave propagating medium such as water or liquid paraffin through the distal end 24 provided with the ultrasonic vibrating element 21, and a cooling capacity control section 37 controls a cooling capacity for an ultrasonic wave propagating medium of a cooling device 38.

The circulating pump 36 and the cooling device 38 are provided outside the endoscope. The ultrasonic wave propagating medium is circulated through the distal end 24 via an inlet passage 39 and an outlet passage 40 formed in the insertion section and extending therethrough, as shown in FIG. 3. The cooling device 38 and the inlet passage 39 are connected to each other by an adiabatic tube.

Figure 5:
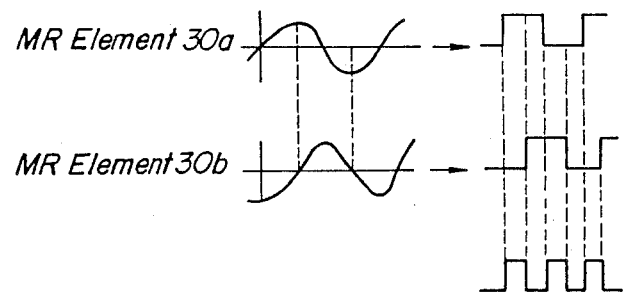
FIG. 5 is a graph of a signal for explaining the operation of the signal processing circuit.

In the above construction, if the ultrasonic vibrating element 21 is rotated through the flexible shaft 25, a magnetic field passing through the MR elements 30a and 30b is changed according to the magnetized pattern of the magnetic recording section 26 provided on the rotating shaft 22a, so that an electric resistance of the MR elements 30a and 30b is changed accordingly. As shown in FIG. 4, since a constant electric current is supplied to the MR elements 30a and 30b from the constant current source 31, the MR elements 30a and 30b generate thereacross voltages corresponding to the change of the magnetic field formed by the magnetized pattern, as shown in FIG. 5. Since the MR elements 30a and 30b are separated by one and a half of the pitch of the magnetized pattern, i.e., if the MR element 30a is offset from the center of a NORTH pole by a ¼ of the pitch, the MR element 30b is offset from the center of an adjacent SOUTH pole in an opposite direction, the phases of the output voltages of the MR elements 30a and 30b are shifted with respect to each other by a ¼ of a period. Therefore, if points crossing a zero level of the output voltages of the MR elements 30a and 30b are detected so that the output voltage signals are converted into pulse signals, and an exclusive OR of the pulse signals is obtained, twice the number of pulses for one pitch rotation of the magnetized pattern of the ultrasonic vibrating element 21 are obtained. The MR element 30c is not subjected to a change of a magnetic field by the magnetized pattern, but senses a change of resistance due to a temperature change of and surrounding the magnetic sensor 27. Since this temperature change is included in the changes of resistance sensed by the MR elements 30a and 30b, by taking differences between an output voltage of the MR element 30c and output voltages of the MR elements 30a and 30b by the differential amplifiers 32a and 32b, respectively, the resistance change component due to the temperature change is canceled out, so that the magnetized pattern can be detected as an electric signal without being affected by the temperature change, and thus a rotation angle of the ultrasonic vibrating element 21 can be accurately sensed. Accordingly, a resistance change of the MR element due to the temperature change is sensed, and a difference between a resistance change due to the magnetized pattern and the resistance change due to the temperature change is obtained, so that an error in detecting the rotation angle due to the temperature change can be remarkably reduced.

The output voltage of the MR element 30c is further processed by the temperature drift sensing circuit 33 and the temperature sensing circuit 34, so that there is derived a voltage change representing the temperature change. This temperature change information is applied to the flow rate control section 35, which controls a flow rate of the circulating pump 36 such that a temperature of the ultrasonic wave propagating medium in the distal end 24 becomes a predetermined temperature. The temperature information sensed by the temperature sensing circuit 34 is also applied to the cooling capacity control section 37, which controls a cooling capacity of the cooling device 38 such that a temperature of the ultrasonic wave propagating medium in the distal end 24 becomes a predetermined temperature.

This, in the rotation sensor having the MR elements 30a and 30b, by using an output voltage of the MR element 30c for canceling a temperature drift component, a temperature of the distal end 24 can be sensed without providing a specific temperature sensor, and thus a temperature of an ultrasonic wave propagating medium circulating through the distal end 24 can be controlled.

FIG. 6 shows a second embodiment of the ultrasonic endoscope apparatus according to the invention. In this embodiment, rotating shaft 22 is provided on only one end face of the ultrasonic vibrating element 21. The magnetic recording section 26 on which NORTH and SOUTH poles are alternatively magnetized along a circumferential direction of the shaft 22 similar to the first embodiment is provided on the rotating shaft 22, and the magnetic sensor 27 is fixedly disposed near the magnetic recording section 26.

FIGS. 7A and 7B show a third embodiment of the ultrasonic endoscope apparatus according to the present invention. In this embodiment, the magnetic recording section 26, on which NORTH and SOUTH poles similar to the first embodiment are alternatively magnetized along a circle coaxial to the rotating shaft 22, is provided on one end face of the ultrasonic vibrating element 21, and the magnetic sensor 27 is fixedly disposed near the magnetic recording section 26.

FIG. 8 shows a construction of the main part of a fourth embodiment of the ultrasonic endoscope apparatus according to the present invention. In this embodiment, rotating shafts 22a and 22b are projected from both end faces of the ultrasonic vibrating element 21 and rotatably housed in the distal end 24 of the endoscope insertion section by bearings 23a and 23b. A rotation angle sensing mechanism constructed on and around the shaft 22a has the same construction as the above described first embodiment. The rotating shaft 22b is connected to one shaft of a motor 39 for driving the rotation thereof. The other shaft of the motor 39 is fixed to a rotor 40a of a rotary transformer 40. A stator 40b of the rotary transformer is rotatably provided on the same shaft, coaxially to the rotor 40a, through bearings 41a and 41b.

In this embodiment, different from the above described first embodiment, the ultrasonic vibrating element 21 is rotated by the motor 39 housed in the distal end 24. An ultrasonic wave transmitting signal for driving the vibrating element 21 and an ultrasonic wave receiving signal generated when an ultrasonic signal is received are transmitted through the rotary transformer 40 wherein the rotor 40a and the stator 40b are not in contact with each other.

Thus, also in this case, in which the drive source for rotating the ultrasonic vibrating element is provided in the distal end 24 of the endoscope insertion section, a rotation angle of the ultrasonic vibrating element must be sensed, and therefore, the effect of this embodiment is the same as of the other embodiments.

Note that the present invention is not restricted to the above described embodiments, but many modifications or variations can be made. For example, although the magnetized pattern of the magnetic recording section 26 is sensed by the two MR elements 30a and 30b in the above embodiments, the magnetized pattern may be sensed by only one MR element. Although, in the above described embodiment, the magnetic recording section 26 is rotated integrally with the ultrasonic vibrating element 21 and the magnetic sensor 27 including the MR element is fixedly provided, the magnetic sensor can be constructed in such a manner that a plurality of MR elements are formed with a predetermined pattern along the rotating direction so as to rotate integrally with the ultrasonic vibrating element 21, so that the magnetic recording section is fixedly disposed near this magnetic sensor to sense a rotation angle of the ultrasonic vibrating element. Further, although, in the above described embodiment the MR element 30c for sensing the temperature drift component is provided so that the temperature drift component of the MR elements 30a and 30b sensing the magnetized pattern of the magnetic recording section 26 is rectified, and a temperature of the ultrasonic wave propagating medium circulated through the distal end 24 is controlled, these controls are not essential. The present invention can be applied not only to an ultrasonic endoscope apparatus including an optical or electronical type observing system but also to an ultrasonic endoscope apparatus without an optical type observing system.

As described above, according to the present invention, since the magnetic recording section and the magnetic sensor are provided near the ultrasonic vibrating element in such a manner that one of the magnetic recording section and the magnetic sensor is rotated integrally with the ultrasonic vibrating element, a rotation angle of the ultrasonic vibrating angle is directly sensed and is not affected by an influence of a phase shift of a rotation angle due to a torsion of the flexible shaft or a friction between the flexible shaft and inner wall of the guide tube. Therefore, a direction of a scanning line of a picked-up ultrasonic image and a direction of an ultrasonic beam are exactly coincided with each other, and the shape of the picked up object is accurately displayed without any distortion. Since a small magnetic type rotary encoder is constructed by the magnetic recording section and the magnetic sensor including the MR element, these components can be effectively housed in a narrow space without enlarging the distal end of the endoscope. Further, since an image of an object is sensed by a non-contact type magnetic sensor, different from the optical type apparatus, the apparatus can be used also in an opaque medium and a rotation load for the ultrasonic vibrating element is only slightly increased. According to the above described embodiments, a flow rate and cooling temperature of a circulating cooling medium (acoustic transmitting medium) is appropriately controlled by sensing a temperature of the distal end by the MR element for compensating the temperature drift, so that the temperature of the distal end can be maintained exactly at a target temperature (a temperature of a human body). Therefore, the patient is not subjected to pain, and an appropriate measure can be taken against a sudden generation of heat from the ultrasonic vibrating element, so that the ultrasonic endoscope apparatus according to the invention is advantageous from the view point of safety.

What is claimed is:

1. An ultrasonic endoscope apparatus having an elongated insertion section, a distal end of which is inserted in an object to be inspected, said ultrasonic endoscope apparatus comprising:

an ultrasonic vibrating element rotatably housed in said distal end, said ultrasonic vibrating element radiating an ultrasonic wave to obtain an image of said object;

means for rotating said ultrasonic vibrating element about a rotation axis;

a magnetic recording section provided in said distal end, said magnetic recording section having a given pattern of magnetization for forming a magnetic field; and a magnetic sensor having at least one magneto-resistive element for sensing said magnetic field;

means for mounting at least one of said recording section and magnetic sensor so that it rotates integrally with said ultrasonic vibrating element to cause said magnetic sensor to sense a change of said magnetic field representing a rotation angle of said ultrasonic vibrating element.

2. An ultrasonic endoscope apparatus according to claim 1, wherein said rotating means comprises a flexible shaft extending through said insertion section, and means for supplying a rotary motion, one end of said flexible shaft being connected to said means for supplying rotary motion and the other end of said flexible shaft being connected to said ultrasonic vibrating element.

3. An ultrasonic endoscope apparatus according to claim 1, wherein said rotating means comprises a motor housed in said distal end and connected to said ultrasonic vibrating element.

4. An ultrasonic endoscope apparatus according to claim 1, wherein said magnetic recording section rotates together with said ultrasonic vibrating element.

5. An ultrasonic endoscope apparatus according to claim 4, wherein said ultrasonic vibrating element has opposite end faces and rotating shafts coaxially projecting from said opposite end faces, said magnetic recording section being provided on one of said rotating shafts.

6. An ultrasonic endoscope apparatus according to claim 4, wherein said ultrasonic vibrating element has only one rotating shaft projecting from an end face of said element, and said magnetic recording section is provided on said one rotating shaft.

7. An ultrasonic endoscope apparatus according to claim 1, wherein said magnetic recording section is provided on an end face of said ultrasonic vibrating element.

8. An ultrasonic endoscope apparatus according to claim 1, wherein said given pattern of magnetization of said magnetic recording section is formed by magnetizing a magnetic material to alternatively form a NORTH pole and a SOUTH pole with a pitch along a rotational direction of said ultrasonic vibrating element.

9. An ultrasonic endoscope apparatus according to claim 8, wherein said magnetic sensor has two magneto-resistive elements which are separated from each other by a distance corresponding to one and a half of said pitch.

10. An ultrasonic endoscope apparatus according to claim 1, wherein said magnetic sensor has a magneto-resistive element made of ferromagnetic material.

11. An ultrasonic endoscope apparatus according to claim 10, wherein said magnetic sensor has a glass substrate on which said magneto-resistive element is applied.

12. An ultrasonic endoscope apparatus according to claim 1, further comprising means for sensing a temperature of and surrounding said magnetic sensor and means responsive to a sensed temperature for controlling at least one characteristic of an ultrasonic wave propagating medium flowing through said distal end.

13. An ultrasonic endoscope apparatus according to claim 12, wherein said temperature sensing means comprises a sub magneto-resistive element provided on a portion whereat said magnetic field made by magnetization has no effect, said sub magneto-resistive element sensing a drift component of an electric signal due to a temperature variation.

14. An ultrasonic endoscope apparatus according to claim 12, wherein said means for controlling comprises a pump circulating said ultrasonic wave propagating medium through said distal end, and a flow rate control section controlling a flow rate of said medium by said pump according to said temperature.

15. An ultrasonic endoscope apparatus according to claim 14, further comprising a cooling device for cooling said ultrasonic wave propagating medium, and a cooling capacity control section for controlling a cooling capacity of said device according to said temperature.

* * * * *